(12) United States Patent
Zhan et al.

(10) Patent No.: US 11,728,009 B2
(45) Date of Patent: Aug. 15, 2023

(54) SYSTEM AND PROCESS FOR DATA-DRIVEN DESIGN, SYNTHESIS, AND APPLICATION OF MOLECULAR PROBES

(71) Applicant: Fusion Genomics Corporation, Burnaby (CA)

(72) Inventors: Shing H. Zhan, Burnaby (CA); Brian S. Kwok, Burnaby (CA); Mohammad A. Qadir, Burnaby (CA)

(73) Assignee: FUSION GENOMICS CORPORATION, Burnaby (CA)

( * ) Notice: Subject to any disclaimer, the term of this patent is extended or adjusted under 35 U.S.C. 154(b) by 1173 days.

(21) Appl. No.: 16/081,879

(22) PCT Filed: Mar. 1, 2017

(86) PCT No.: PCT/CA2017/050273
§ 371 (c)(1),
(2) Date: Aug. 31, 2018

(87) PCT Pub. No.: WO2017/147702
PCT Pub. Date: Sep. 8, 2017

(65) Prior Publication Data
US 2019/0080049 A1  Mar. 14, 2019

Related U.S. Application Data

(60) Provisional application No. 62/302,078, filed on Mar. 1, 2016.

(51) Int. Cl.
*G16B 30/00* (2019.01)
*C12N 15/10* (2006.01)
(Continued)

(52) U.S. Cl.
CPC ............ *G16B 30/00* (2019.02); *C07H 21/04* (2013.01); *C12N 15/10* (2013.01);
(Continued)

(58) Field of Classification Search
CPC ........ G16B 30/00; G16B 30/10; G16B 25/20; G16B 25/00; G16B 50/00; C07H 21/04; C12N 15/10; C12Q 1/6806
(Continued)

(56) References Cited

U.S. PATENT DOCUMENTS

2007/0259337 A1* 11/2007 Hully .................... C12Q 1/701
435/5

OTHER PUBLICATIONS

Gerasimova,Yulia V. Kolpashchikov, Dmitry M.: "Nucleic Acid Detection using MNAzymes", Chemistry & Biology 17, Feb. 26, 2010 (Year: 2010).*

(Continued)

*Primary Examiner* — G Steven Vanni
*Assistant Examiner* — Guozhen Liu
(74) *Attorney, Agent, or Firm* — Leason Ellis LLP (57) ABSTRACT

The disclosure provides methods and systems for designing and synthesizing probes to capture a representative sample of genomic variants of a target genome from a sample. The methods include providing a multiple sequence alignment (MSA), designing a plurality of representative subsequences, and optionally synthesizing a nucleic acid probe. The designing step can comprise designating a plurality of intervals in the MSA, shifting start positions for each MSA subset, clustering the aligned subsequences within each adjusted subset, and determining a representative sequence for each reduced MSA subset. The disclosure also encompasses methods of isolating a plurality of nucleic acid variants of a targeted genomic subregion from a sample using the disclosed probe design, as well as the probe compositions themselves.

16 Claims, 5 Drawing Sheets
Specification includes a Sequence Listing.

(51) Int. Cl.
*G16B 25/00* (2019.01)
*G16B 25/20* (2019.01)
*G16B 50/00* (2019.01)
*C12Q 1/6806* (2018.01)
*G16B 30/10* (2019.01)
*C07H 21/04* (2006.01)
*C40B 30/04* (2006.01)

(52) U.S. Cl.
CPC ..... *C12N 15/1003* (2013.01); *C12N 15/1089* (2013.01); *C12Q 1/6806* (2013.01); *C40B 30/04* (2013.01); *G16B 25/00* (2019.02); *G16B 25/20* (2019.02); *G16B 30/10* (2019.02); *G16B 50/00* (2019.02)

(58) Field of Classification Search
USPC .......................................................... 702/19
See application file for complete search history.

(56) References Cited

OTHER PUBLICATIONS

Andreas Untergasser, Ioana Cutcutache, Triinu Koressaar, Jian Ye, Brant C. Faircloth, Maido Remm and Steven G. Rozen: "Primer3—new capabilities and interfaces", Nucleic Acids Research, 2012, vol. 40, No. 15 e115, Published online Jun. 22, 2012 (Year: 2012).*
Brodin, J. et al. A multiple-aligmnent based primer design algorithm for genetically highly variable DNA targets. BMC Bioinformatics. Aug. 21, 2013 (Aug. 21, 2013), vol. 14:255.
Broude, N.E. et al. Stem-loop oligonucleotides: a robust tool for molecular biology and biotechnology. TRENDS in Biotechnology. Jun. 2002 (Jun. 2002), vol. 20(6):249-56.
Carreno-Duran, L.R. et al. Design of a set of probes with high potential for influenza virus epidemiological surveillance. Bioinformation. Apr. 30, 2013 (Apr. 30, 2013), vol. 9, No. 8, p. 414-20.
Do CB, Mahabhashyam MSP, Brudno M, and Batzoglou S. 2005. PROBCONS: Probabilistic Consistency-based Multiple Sequence Alignment. Genome Res 15:330-40.
Edgar RC. 2004. MUSCLE: multiple sequence alignment with high accuracy and high throughput. Nucleic Acids Research 32:1792-7.
Guerrero, D. et al. AlignMiner: a Web-based tool for detection of divergent regions in multiple sequence aligmnents of conserved sequences. Algorithms for Molecular Biology. Jun. 2, 2010 (Jun. 2, 2010), vol. 5:24.
Hueman Jaimes-Diaz et al: "In Silico Genomic Fingerprints of the Bacillus anthracis Group Obtained by Virtual Hybridization", MICROARRAYS, vol. 4, No. 1, Mar. 1, 2015 (Mar. 1, 2015), pp. 84-97, XP055637813, ISSN: 2076-3905, DOI: 10.3390/microarrays4010084.
Hueman Jaimes-Diaz et al: "Bacterial classification using genomic fingerprints obtained by virtual hybridization", Journal of Microbiological Methods, Elsevier, Amsterdam, NL, vol. 87, No. 3, Aug. 24, 2011 (Aug. 24, 2011), pp. 286-294, XP028109157, ISSN: 0167-7012, DOI: 10.1016/J.MIMET.2011.08.014.
Vshina A et al: "Mapping of genomic segments of influenza B virus strains by an oligonucleotide microarray method.", J Clin Microbiol., Dec. 31, 2004 (Dec. 31, 2004), pp. 5793-5801, XP055637820.
Katoh K, Standley DM. 2013. MAFFT multiple sequence alignment software version 7: improvements in performance and usability. Mol Biol Evol 30:772-80.
Langmead B, Salzberg SL. 2012. Fast gapped-read alignment with Bowtie 2. Nat Methods 9:357-9.
Larkin MA, et al. 2007. ClustalW and ClustalX version 2. Bioinformatics 23: 2947-8.
Li H, Durbin R. 2009. Fast and accurate short read alignment with Burrows-Wheeler Transform. Bioinformatics 25:1754-60.
International Preliminary Report on Patentability dated Sep. 4, 2018, in respect of corresponding International Patent Application No. PCT/CA2017 /050273.
Extended European Search Report dated Nov. 27, 2019, in respect of corresponding European Patent Application No. 17759041.1.
Communication under Article 94(3) dated Oct. 20, 2020, in respect of corresponding European Patent Application No. 17759041.1.
English translation of First Office Action dated Jun. 8, 2021, issued in respect of corresponding Chinese Patent Application No. 201780024591.8.
Communication pursuant to Article 94(3) EPC dated Aug. 4, 2021, issued in respect of corresponding European Patent Application No. 17 759 041.1.
Second Office Action dated Feb. 17, 2022, issued in respect of corresponding Chinese Patent Application No. 201780024591.8.
English Summary of Second Office Action dated Feb. 17, 2022, issued in respect of corresponding Chinese Patent Application No. 201780024591.8.
Notification of Rejection for corresponding Chinese Application No. 201780024591.8, dated Sep. 6, 2022.
Examiner's Report issued in corresponding Canadian Patent Application No. 3,016,222, dated Mar. 14, 2023.

* cited by examiner

SEQUENCE LISTING

<160> NUMBER OF SEQ ID NOS: 5

<210> SEQ ID NO 1
<211> LENGTH: 26
<212> TYPE: DNA
<213> ORGANISM: Artificial sequence
<220> FEATURE:
<223> OTHER INFORMATION: Synthetic

<400> SEQUENCE: 1
atggtgatta gcacagatcg gactca					26

<210> SEQ ID NO 2
<211> LENGTH: 26
<212> TYPE: DNA
<213> ORGANISM: Artificial sequence
<220> FEATURE:
<223> OTHER INFORMATION: Synthetic

<400> SEQUENCE: 2
atgctgctta gcacagctcg ggctga					26

<210> SEQ ID NO 3
<211> LENGTH: 26
<212> TYPE: DNA
<213> ORGANISM: Artificial sequence
<220> FEATURE:
<223> OTHER INFORMATION: Synthetic

<400> SEQUENCE: 3
atggtgatta gcacacatgg agctga					26

<210> SEQ ID NO 4
<211> LENGTH: 26
<212> TYPE: DNA
<213> ORGANISM: Artificial sequence
<220> FEATURE:
<223> OTHER INFORMATION: Synthetic

<400> SEQUENCE: 4
acggtgatta gcacagatcg tactct					26

<210> SEQ ID NO 5
<211> LENGTH: 25
<212> TYPE: DNA
<213> ORGANISM: Artificial sequence
<220> FEATURE:
<223> OTHER INFORMATION: Synthetic

<400> SEQUENCE: 5
atggtgctag cacatatcgg actca					25

SYSTEM AND PROCESS FOR DATA-DRIVEN DESIGN, SYNTHESIS, AND APPLICATION OF MOLECULAR PROBES

CROSS-REFERENCE TO RELATED APPLICATION

This application claims the benefit of U.S. Provisional Application No. 62/302,078, filed Mar. 1, 2016, the disclosure of which is incorporated herein by reference in its entirety.

FIELD OF THE INVENTION

The disclosure provides methods and systems for the rational design, synthesis, and application of molecular probes.

STATEMENT REGARDING SEQUENCE LISTING

The sequence listing associated with this application is provided in text format in lieu of a paper copy and is hereby incorporated by reference into the specification. The name of the text file containing the sequence listing is 57930 Sequence Final 2017-02-28.txt. The text file is 2 KB; was created on Feb. 28, 2017; and is being submitted with the filing of the specification.

BACKGROUND

An early technology to capture known stretches of DNA was Southern blotting. Variants of this technology, including Northern blotting which captures RNA, have been adopted in many modern applications, including microarrays and liquid phase hybridization. Although the DNA capture concept has been updated and applied to many other inventions, the use of complementary DNA sequence-based probes as "baits" has not changed since the early 1970's. This conventional probe design depends on a single template that can be a reference sequence or majority-rule consensus sequence (which is typically computed from available sequence data for a target genetic region). This design approach has remained unchanged since the advent of Southern/Northern blotting, which relies on probe-target molecule binding to signal the presence of target nucleic acids. Although straightforward, this design approach is not always ideal, because it may introduce target capture bias.

Target capture bias occurs when a probe preferentially binds to nucleic acids that are more similar to the probe than others. Traditionally-designed probes are suboptimal in applications where the aim is to capture a representative pool of highly variable nucleic acids. For example, the influenza genome mutates rapidly during an infection, and therefore is manifest as hundreds, if not thousands, of variants inside the infected patient. When used to enrich for highly variable influenza genomes, conventionally designed probes would only capture a subset of the genomes, therefore creating an unrepresentative sampling of the genomes present. To obtain less biased samplings, one may instead resort to using a collection of conventionally designed probes. However, in cases like influenza where the genetic diversity is very high (e.g., with hundreds of thousands of reported strains), an enormous number of reference-based probes is required to completely capture known genetic diversity, because each probe supposedly targets a single strain. Such probe designs are poorly scalable, inefficient, and wasteful.

Before the advent of next-generation sequencing (NGS) technologies, routine identification of highly mutable genetic sequences was impossible. Genetic sequences may exhibit great variability within a single sample or among biologically related samples, often reflective of the underlying biology. Several technologies have been developed to characterize variable genetic sequences; however, none has been successfully applied in the clinical setting.

Sanger sequencing is the de facto gold standard for characterizing genetic sequences, owing to its markedly low error rate. This method, however, depends heavily on polymerase chain reaction (PCR), a chemical reaction that exponentially multiplies a target genetic region. Sanger sequencing performs well on stable genetic regions, in that each base can be determined without signal ambiguity. When it is applied to fast mutating (or highly variable) regions, however, Sanger sequencing suffers from the following shortcomings:

1. Typically, Sanger sequencing determines the most abundant base. For highly variable genetic sequences, less abundant bases may be missed during base calling.
2. It requires primer binding sites to be stable and specific. Therefore, many genetic regions of interest may be too variable for Sanger sequencing to be effective.
3. Primers bind preferentially to genetic sequences that display greater sequence homology to the primers themselves, thereby leading to sequencing bias. NGS technologies enable unbiased genetic sequencing.

Whole metagenome sequencing is a widely used technique to sequence all nucleic acids—from bacterial, viral, and eukaryotic sources—in a clinical or environmental sample. Whole metagenome sequencing studies employing NGS have been revealing previously unknown genetic diversity of bacteria and viruses. This hidden diversity may offer valuable information which has yet to be fully appreciated (for example, information about the within-patient genetic diversity of hepatitis C virus may offer insight into the transmission dynamics of the virus). Although powerful, whole metagenome sequencing using NGS is expensive and may be inefficient, particularly in applications where only a few select genetic regions and/or organisms are of interest.

Targeted metagenome sequencing has been proposed as an alternative to whole metagenome sequencing, when the target organisms and/or genetic regions are predetermined. Targeted sequencing is a general term to describe techniques that sequence only the genetic regions of interest, rather than blindly sequencing all genetic material in a given sample. For example, amplicon NGS of the rRNA gene in bacteria has become a widely employed technique to survey the species composition of environmental samples. The goal of targeted sequencing is to elevate the signal-to-noise ratio (i.e., wanted versus unwanted sequences) in NGS data. Targeting can be achieved using various methods. These methods include gene-specific priming, liquid (or solid) phase hybridization, protein-nucleic acid binding, and enzymatic digestion. Each method has its own strengths, weaknesses, and intended applications. Liquid phase hybridization (LPH) is most relevant to the current disclosure. LPH operates on the principle of nucleic acid complementary binding. LPH of nucleic acid (i.e., DNA or RNA) molecules is a powerful technique when a tractable collection of nucleic acid segments is concerned (for example, in the identification of influenza subtypes and strains). This technique requires the design of small nucleic acids (referred to as probes hereafter; note that in PCR, such probes are referred to as primers) to bind to and enrich for the target genetic regions.

Despite the advances in the art of genome sampling and sequencing technologies, there remains a need for cost-effective and efficient methods for obtaining a comprehensive sampling of a variable genomes within an environment. The present disclosure addresses this and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a method of designing probes for isolating a plurality of nucleic acid variants of a targeted genomic domain. The method comprises:

(a) providing a multiple sequence alignment (MSA) of nucleic acid sequences of observed variants of the targeted genomic domain; and (b) designing a plurality of representative subsequences, wherein the designing step comprises:
  (i) designating a plurality of intervals within the length of the MSA, wherein each interval consists of an MSA subset with aligned nucleic acid subsequences of the observed variants, and wherein each MSA subset has a distinct start position;
  (ii) independently shifting the start position for each MSA subset within the MSA by a designated number of nucleic acid positions and in a designated direction to provide an adjusted MSA subset with aligned adjusted nucleic acid subsequences of the observed variants;
  (iii) optionally, independently assessing each adjusted MSA subset for conformance to a termination criterion and repeating step (ii) if an adjusted MSA does not conform to the termination criterion;
  (iv) independently clustering the aligned nucleic acid subsequences within each adjusted MSA subset to provide a reduced MSA subset corresponding to each adjusted MSA subset; and
  (v) determining a representative subsequence for each reduced MSA subset.

In some embodiments, the method also comprises the step of synthesizing at least one nucleic acid probe corresponding to each reduced MSA subset, wherein each nucleic acid probe comprises the representative subsequence, or the complement thereof, representing the respective distilled MSA subset.

In one embodiment, the plurality of intervals within the length of the MSA are designated according to defined spatial constraints. In one embodiment, the designated intervals are distributed uniformly across the length of the MSA. In one embodiment, the plurality of intervals within the length of the MSA are designated in areas that contain above average conservation within the MSA. In one embodiment, at least two of the plurality of representative subsequences are non-overlapping. In one embodiment, the plurality of intervals in step (b)(i) are designated randomly. In one embodiment, the designating of step (b)(i) comprises extracting the MSA subsets from the plurality of designated intervals to provide the aligned nucleic acid subsequences within each designated interval. In one embodiment, the start position of each MSA subset is a position that is at the 5' end or the 3' end of the subset. In one embodiment, the designated number of nucleic acid positions by which each MSA subset start position is shifted does not exceed the length of the respective MSA subset. In one embodiment, the start position of each MSA subset is shifted in the 5' direction. In one embodiment, the start position of each MSA subset is shifted in the 3' direction. In one embodiment, the designated number of nucleic acid positions and/or the designated direction for independently shifting each MSA subset increases the number of conserved positions within the adjusted MSA subset. In one embodiment, the adjusted MSA subsets resulting from the shifting of step (b)(ii) conform to defined spatial constraints. In one embodiment, the designated number of nucleic acid positions and/or the designated direction for independently shifting each MSA subset increases the placement of the conserved positions within a center region of the adjusted MSA subset. In one embodiment, the termination criterion of step (b)(iii) comprises a preset number of shift iterations, a preset percentage of conserved positions within the adjusted MSA subset, a preset threshold for positioning of conserved positions, and the like. In one embodiment, the clustering of step (b)(iv) comprises grouping the adjusted nucleic acid subsequences of each adjusted MSA subset by similarity using a distance metric to provide one or more groups of adjusted nucleic acid subsequences for each adjusted MSA subset. In a further embodiment, the clustering of step (b)(iv) further comprises ranking the one or more groups of adjusted nucleic acid subsequences for each adjusted MSA subset according to size as defined by number of adjusted nucleic acid subsequences. In one embodiment, the reduced MSA subset consists of the one or more groups of adjusted nucleic acid subsequences for each adjusted MSA that meet or exceed a preset size threshold. In one embodiment, the representative sequence is determined by denoising the reduced MSA subset of any spurious variants. In one embodiment, the representative sequence is a consensus sequence for the corresponding reduced MSA subset. In one embodiment, the representative sequence for each reduced MSA subset is screened in silico against a database of known nucleic acid sequences, wherein any representative sequence that demonstrates high similarity to a known sequence irrelevant to the target genomic domain is omitted from further steps in the method. In one embodiment, the sequences of the MSA are first transformed to have the same length by inserting gaps in the shorter sequences in a manner that enhances alignment of homologous nucleic acids in the MSA. In one embodiment, the nucleic acid probe comprises the representative sequence, or the complement thereof, is not continuous within the nucleic acid probe. In one embodiment, the representative sequence (e.g., consensus sequence), or the complement thereof, within the nucleic acid probe is interrupted by a sequence that facilitates formation of a hairpin structure.

In another aspect, the disclosure provides a method of isolating a plurality of nucleic acid variants of a targeted genomic subregion from a sample. The method comprises contacting a plurality of probes to the sample, wherein each probe comprises a representative subsequence sequence, or the complement thereof, of a reduced MSA subset; and isolating the nucleic acid molecules in the sample that hybridize to one or more probes of the plurality of probes. In one embodiment, the plurality of probes is obtained by the following steps:

(a) providing a multiple sequence alignment (MSA) of nucleic acid sequences of observed variants of the targeted genomic domain; and (b) designing a plurality of representative sequences, comprising:

(i) designating a plurality of intervals within the length of the MSA, wherein each interval consists of an MSA subset with aligned nucleic acid subsequences of the predicted variants, and wherein each MSA subset has a distinct start position;

(ii) independently shifting the start position for each MSA subset within the MSA by a designated number of nucleic acid positions and in a designated direction to provide an adjusted MSA subset with aligned adjusted nucleic acid subsequences of the observed variants;

(iii) optionally, independently assessing each adjusted MSA subset for conformance to a termination criterion and repeating step (ii) if an adjusted MSA does not conform to the termination criterion;

(iv) independently clustering the aligned nucleic acid subsequences within each adjusted MSA subset to provide a reduced MSA subset corresponding to each adjusted MSA subset; and    (v) determining a representative subsequence for each distilled MSA subset; and In one embodiment, the method further comprises synthesizing the plurality of probes.

In one embodiment, each representative sequence is included in at least one probe within the plurality of probes. In one embodiment, the method further comprises sequencing the nucleic acid molecules isolated from the sample.

In another aspect, the disclosure provides one or more nucleic acid probes synthesized by the method disclosed herein. In one embodiment, the targeted genomic domain is selected from an HA domain and NA domain of influenza virus.

In another aspect, the disclosure provides a nucleic acid probe comprising a first target domain, a second target domain, and a hairpin domain disposed between the first target domain and the second target domain, wherein the hairpin domain forms a hairpin structure that results in the first target domain and the second target domain aligning in close proximity such that together they are capable of hybridizing to a continuous complementary target sequence. In one embodiment, the hairpin domain further comprises a ligand attached thereto. In one embodiment, the hairpin domain further comprises restriction enzyme digestion site. In one embodiment, the first target domain and the second target domain are designed by the methods described herein.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIGS. 5A and 5B illustrate two representative embodiments of physical probes constructed from the design provided by the disclosed method and system.

DETAILED DESCRIPTION

The present disclosure relates to methods and systems for rationally designing probes that can efficiently and comprehensively sample highly variable genomes. The rational design utilizes available sequence data to capture genetic region(s) of interest. In contrast to existing methods, such as naively creating a probe for each distinct variant of the genetic region (or each strain in the example of influenza), the disclosed method derives a minimal set of probes that (1) minimizes target capture bias and (2) maximizes coverage of target genetic diversity. The disclosure is based on the inventors' development of a system and process for designing probes from sequence data, synthesizing the probes, and finally applying the probes to problems addressable by targeted sequencing. The inventors have also demonstrated the utility and performance of these rationally designed probes by using them to capture variable genomes from viruses, such as influenza, directly from clinical samples.

One application of the disclosed methods and systems is the capture of targeted genetic material (i.e., target enrichment). The methods and systems, however, can be used to deplete or remove unwanted genetic material. Additionally, the probes designed using the disclosed approach can be coupled with any nucleic acid detection technology. For example, while the technology is described in the context of NGS applications, it will be readily apparent that the disclosed approach can also be used to generate probes that are applicable, for example, to microarrays and microfluidics technologies.

Figure 1:
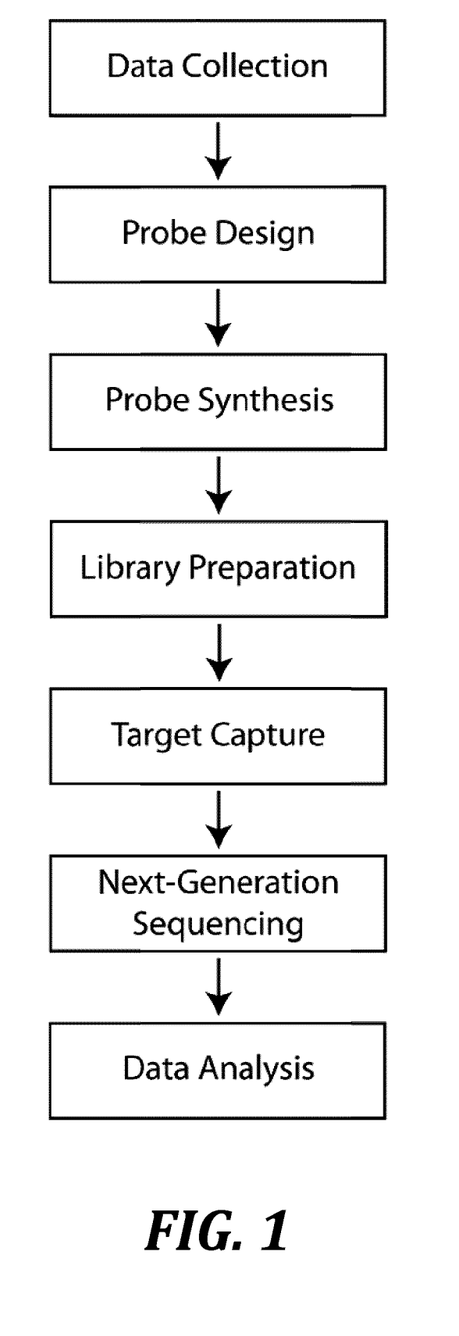
FIG. 1 schematically illustrates an overview of an illustrative approach that utilizes the disclosed methods and systems in a broader strategy to sample and profile the diversity of genomic variants of a target organism from a particular environment.

To illustrate the potential applicability, the disclosed systems, methods, and/or probes generated therefrom, can be integrated into a broader strategy to sample and profile the diversity of genomic variants of a target organism in a particular environment. FIG. 1 provides a schematic overview of such an approach.

One novel aspect of this disclosure is the design of probes using available sequence data and machine learning techniques. This differs from conventional designs that rely on single reference or consensus sequences. Instead, probe designs built using the disclosed approach incorporates information about the genetic diversity of the target region. The result is reduced potential target capture bias and maximum coverage of the target region's genetic diversity. This approach can also utilize machine learning techniques to determine the minimal number of probes needed without sacrificing coverage of genetic diversity. Thus, probes designed using the disclosed approach can offer superior target capture performance compared to conventionally designed probes, particularly in applications where highly variable nucleic acids are concerned (for example, influenza virus genomes that evolve quickly).

In accordance with the foregoing, in one aspect, the present disclosure provides a method of designing and/or synthesizing probes useful for isolating a plurality of nucleic acid variants of a targeted genomic domain. In some embodiments, the method comprises (a) providing a multiple sequence alignment (MSA) of nucleic acid sequences of observed variants of the targeted genomic domain; and (b) designing a plurality of representative subsequences.

The MSA can be generated according to any appropriate method, many of which are commonly used in the art. See additional discussion of illustrative embodiments below. In some embodiments, the generation of an MSA includes inserting gaps within specific sequences to enhance the alignment.

In some embodiments, the method further comprises a step of (c) synthesizing at least one nucleic acid probe corresponding to each reduced MSA subset, wherein each nucleic acid probe comprises the representative subsequence, or the complement thereof, representing the respective distilled MSA subset.

In some embodiments, the step of designing a plurality of representative subsequences (part (b)), comprises:

(i) designating a plurality of intervals within the length of the MSA, wherein each interval consists of an MSA subset with aligned nucleic acid subsequences of the observed variants, and wherein each MSA subset has a distinct start position;

(ii) independently shifting the start position for each MSA subset within the MSA by a designated number of nucleic acid positions and in a designated direction to provide an adjusted MSA subset with aligned adjusted nucleic acid subsequences of the observed variants;

(iii) optionally, independently assessing each adjusted MSA subset for conformance to a termination criterion and repeating step (ii) if an adjusted MSA does not conform to the termination criterion;

(iv) independently clustering the aligned nucleic acid subsequences within each adjusted MSA subset to provide a reduced MSA subset corresponding to each adjusted MSA subset; and (v) determining a representative subsequence for each distilled MSA subset.

The plurality of intervals within the length of the MSA can be designated according to defined spatial constraints or can be arbitrarily assigned based on prior knowledge about the target region. The most basic spatial constraints include the end boundaries of the MSA itself (i.e., the intervals are entirely within the MSA). Other potential spatial constraints include collisions or a minimum distance between adjacent intervals.

Each interval consists of a subset of the MSA. The term "interval" refers specifically to the horizontal length of the selected region of the MSA. The term MSA subset can be used interchangeably with the term "slice," and refers to the alignment of the multiple sequences substrings within the interval (e.g., alignment of substring 1, substring 2, substring 3, etc.). See FIG. 2 for an illustration of several non-overlapping intervals that contain "slices" of an illustrative MSA. In some embodiments, the designated intervals are distributed uniformly (or substantially uniformly) across the length of the MSA. In other embodiments, the distribution can be biased, for instance, towards regions displaying high variability that could benefit from higher probe coverage or away from unwanted regions. In some embodiments, the plurality of intervals within the length of the MSA are designated in areas that exhibit conservation (e.g., above average conservation) within the MSA. In some embodiments, at least two of the plurality of intervals are non-overlapping. In some embodiments, all of the plurality of intervals are non-overlapping. In some embodiments, each of the plurality of intervals has a distinct "starting point". The term "starting point" can be defined as the left- or 5'-most position in the sequence. Alternatively, the term "starting point" can be defined as the right- or 3'-most position in the sequence. Each interval (or MSA subset therein) can have a specified length, which can vary from interval to interval.

According to one embodiment, once the plurality of intervals are designated, each interval is shifted a designated number of nucleic acid positions along the length of the MSA in a designated position to provide an adjusted MSA subset with aligned adjusted nucleic acid subsequences of the variants. The shifting of each interval is independent such that each interval can be shifted according to the same or different criteria. Criteria include a shift of the starting point by a certain number of nucleic acid positions. The shift can also include a similar shift of the corresponding end positions such that the shift results in a sliding "window" over the MSA where the adjusted interval retains the same length. In other embodiments, the end position is shifted, but not over the same number of positions, such that the size of the interval increases or decreases. Finally, in some embodiments, the end position remains static as the starting point is adjusted. The shifts can be either in the 5' or 3' direction (for the starting point and/or the end point).

Aspects of the shifts, including the number of positions, the choice of shifting the starting and/or end positions, and/or the direction thereof, can be implemented to increase the number of conserved positions within the newly formed adjusted MSA subset (i.e., adjusted "slice"). In one embodiment, the shift is implemented in one or more interval to distribute the conserved positions in a manner weighted to a center region of the adjusted MSA subset (e.g., within the middle 50% or so positions rather than the first or last 25% or so positions). Alternatively, the criteria for shifting can also be implemented such that the adjusted MSA subsets conform to defined spatial constraints, such as a minimum distance between adjacent intervals.

In some embodiments, the adjusted MSA subset (adjusted "slices") from the adjusted intervals are each, independently, assessed for conformance to a termination criterion. The termination criterion can include any desirable characteristic of an MSA subset, such as content of conserved nucleic acids, omission of particular common sequence motifs, sequence entropy, GC content, and the like. If a particular adjusted MSA subset does not conform to the termination criterion, the interval can be further adjusted to provide another adjusted MSA subset that is revaluated. This cycle can be repeated as many times as necessary until the preferred criterion is achieved for the adjusted MSA subset. In some embodiments, the number of shift operations can be limited.

It will be understood that as individual intervals are adjusted, several of the resulting adjusted intervals may become overlapping or experience a change in positioning relative to each other.

Once the intervals have been adjusted, a clustering step can be performed on the subsequences of each adjusted MSA subset (adjusted "slice"). This clustering step produces a reduced MSA subset. The reduced MSA subset can be the MSA subset itself, or in some embodiments, the members of a reduced MSA subset are more similar to each other than the other (excluded) members of the MSA subset from the adjusted interval. For example, the reduced MSA subset can omit stochastic variants, which have been flagged as noise (i.e., unrepresentative outlier sequences). Again, for example, rare variants occurring at less than 0.1% frequency can be discarded or ignored. Subsequently, a representative sequence can be determined for each reduced MSA subset. A "representative sequence" refers to a single sequence that represents the majority of sequences present in the reduced MSA subset. The representative sequence can be a consensus sequence, as determined by any appropriate technique generally known in the art for such a purpose. See, e.g., the discussion provided in more detail below. The representative sequence can contain degeneracies at one or more positions, i.e., positions where the identity of the residue remains a limited selection of multiple possible alternative identities (e.g., A/T, G/T, C/G/A, N (any nucleotide), etc.). In some embodiments, the degeneracies can be designated with distribution information, such as at position X, the base is A 20% of the time, T 20% of the time, G 50% of the time, and C 10% of the time.

In some embodiments, the clustering comprises grouping the adjusted nucleic acid subsequences of each adjusted MSA subset by similarity using a distance metric to provide one or more groups of adjusted nucleic acid subsequences for each adjusted MSA subset. In further embodiments, the clustering further comprises ranking the one or more groups of adjusted nucleic acid subsequences for each adjusted MSA subset according to size as defined by number of adjusted nucleic acid subsequences. The reduced MSA subset can then consist of the one or more groups of adjusted nucleic acid subsequences for each adjusted MSA that meet or exceed a preset size threshold.

After the representative sequence(s) is determined, it can be checked for similarity to known nucleic acid sequences to avoid ultimately using probes that would enrich for irrelevant or unrelated sequences. For example, the determined representative sequence(s) for the adjusted MSA subset(s) can be screened in silico against a database of known nucleic acid sequences, wherein any representative sequence that demonstrates high similarity to a known sequence irrelevant to the target genomic domain is omitted from further steps in the method. The threshold of "high similarity" can be readily determined by the theoretical likelihood of hybridization under standard conditions, according to known methods.

Figure 4:
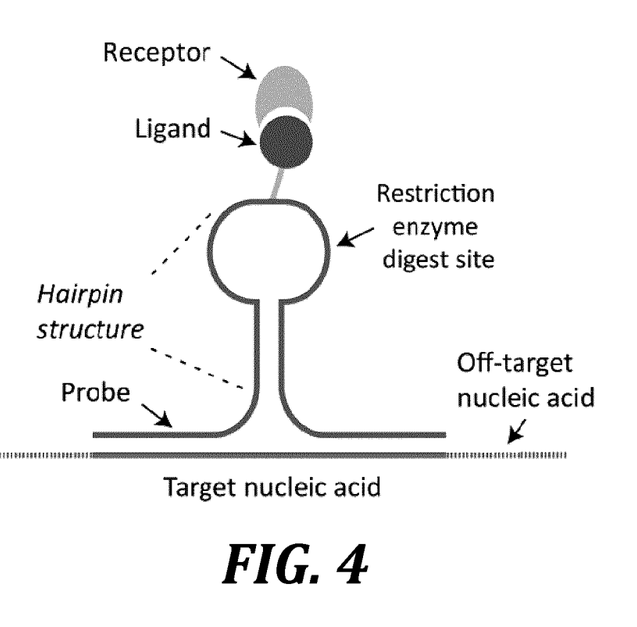
FIG. 4 illustrates an illustrative probe structure that can generated to incorporate the representative sequence provided by the disclosed method, but which incorporates the representative sequence in a non-contiguous manner. In the illustrated embodiment, the representative sequence (as aligned to the target nucleic acid) is divided into two regions and separated by a hairpin structure.
Figure 5A:
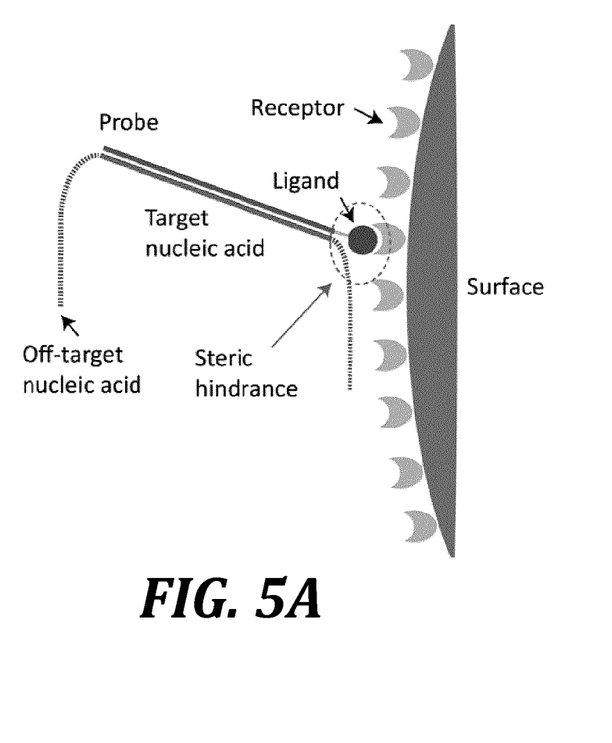
FIG. 5A illustrates an embodiment where the provided sequence is integrated into the probe construct in a single, contiguous sequence.
Figure 5B:
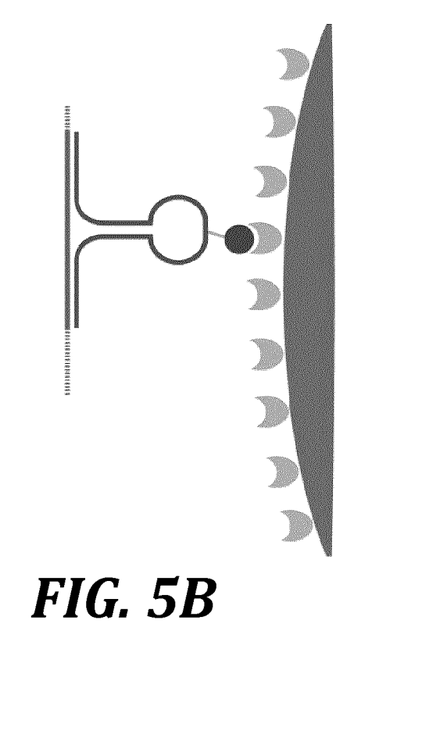
FIG. 5B illustrates an embodiment where the provided sequence is integrated into the probe construct in multiple, discontiguous sequences separated by a hairpin structure.

As indicated, probes can be synthesized or obtained based on the representative sequences obtained in the method described above. It will be appreciated that the probes themselves need not contain the designated representative sequence in one contiguous sequence. Instead, as described below and illustrated in FIGS. 4 and 5B, the probe can contain additional sequence that interrupts the representative sequence, such as additional sequence that forms a hairpin structure. As described below, such a structure can assist the probe construct in enhancing recovery efficiency by permitting the attachment of additional capture reagents (e.g., ligands), while avoiding steric hindrance that may occur if the ligand were attached at a terminus of the probe construct.

The present disclosure also contemplates methods wherein the disclosed probes (comprising representative sequences as described herein, whether or not in a contiguous state) are contacted to a sample, whereby the probes are used to isolate any nucleic acid molecules that hybridize to the representative sequences of the various probes. As described in more detail below, this is demonstrated to successfully enrich for a much higher diversity of target sequence variants than traditional methods relying on standard consensus sequences.

In another aspect, the present disclosure provides molecular probes produced by the method described herein. Representative structures of the probes are described in more detail below. As indicated, the probes can comprise the representative (sub)sequences in a contiguous sequence, or can incorporate domains of the (sub)sequences interrupted by other structures or sequence (such as hairpin structures).

In some embodiments, the probes comprise representative sequences of influenza virus, for example, representative sequences generated from MSAs of the HA or NA domains from the influenza virus strains. Again, the probes need not incorporate the representative sequences in a contiguous state, but can also incorporate interrupted sequences that comprise intervening structure between domains of the representative sequences. Accordingly, the disclosure provides nucleic acid probe comprising a first target domain, a second target domain, and a hairpin domain disposed between the first target domain and the second target domain, wherein the hairpin domain forms a hairpin structure that results in the first target domain and the second target domain aligning in close proximity such that together they are capable of hybridizing to a continuous complementary target sequence In some embodiments, the hairpin domain further comprises a ligand attached thereto. As described below, the ligand can be any known ligand for capture purposes, such as biotin, and the like.

In another aspect, the disclosure provides systems for isolating (enriching) variants of target nucleic acids. The system can comprise probes as described herein that comprise a ligand, as well as a receptor that specifically binds to the ligand. In some embodiments, the receptor is immobilized.

An illustrative embodiment is generally described for context. A sequence database of the genetic region being targeted (e.g., Sanger sequence data for the HA segment of the influenza genome from the NCBI Influenza Virus Resource) is first collated and curated. The aim is to create a set of sequences that are representative of the target genetic region. Optionally, techniques can be used to mitigate sampling biases that may be present. Then, a multiple sequence alignment (MSA) is computed using a multiple sequence aligner, such as MUSCLE (Edgar R C. 2004. MUSCLE: multiple sequence alignment with high accuracy and high throughput. *Nucleic Acids Research* 32:1792-7), MAFFT (Katoh K, Standley D M. 2013. MAFFT multiple sequence alignment software version 7: improvements in performance and usability. *Mol Biol Evol* 30:772-80), or ClustalW (Larkin M A, et al. 2007. ClustalW and ClustalX version 2. *Bioinformatics* 23: 2947-8).

Figure 2:
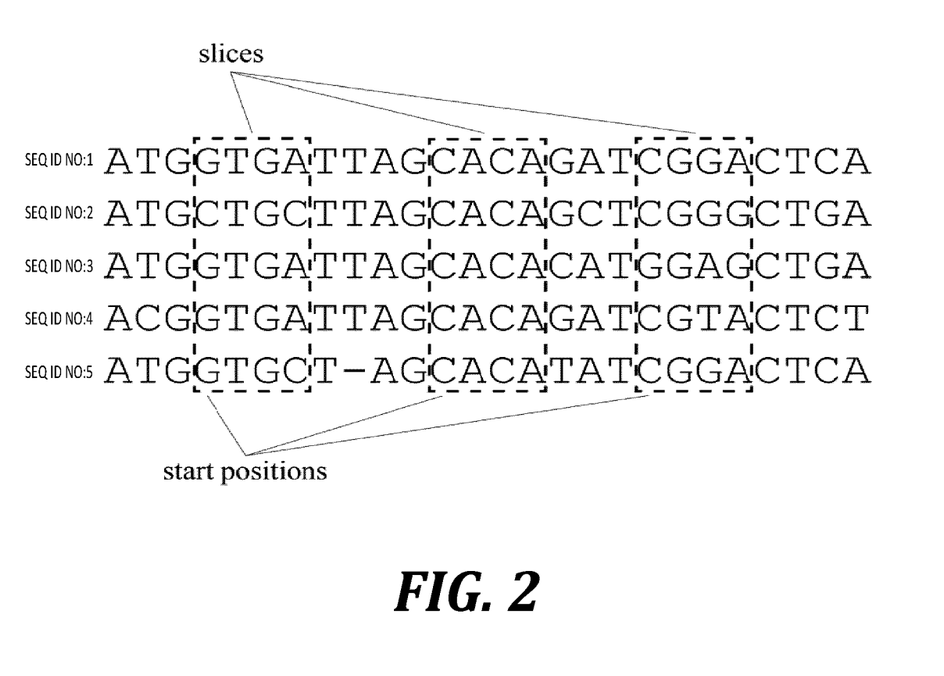
FIG. 2 is an illustrative sequence alignment (MSA) with three designated MSA subsets or "slices." The sequences of the MSA are set forth herein as SEQ ID NOS:1-5, as indicated.
Figure 3:
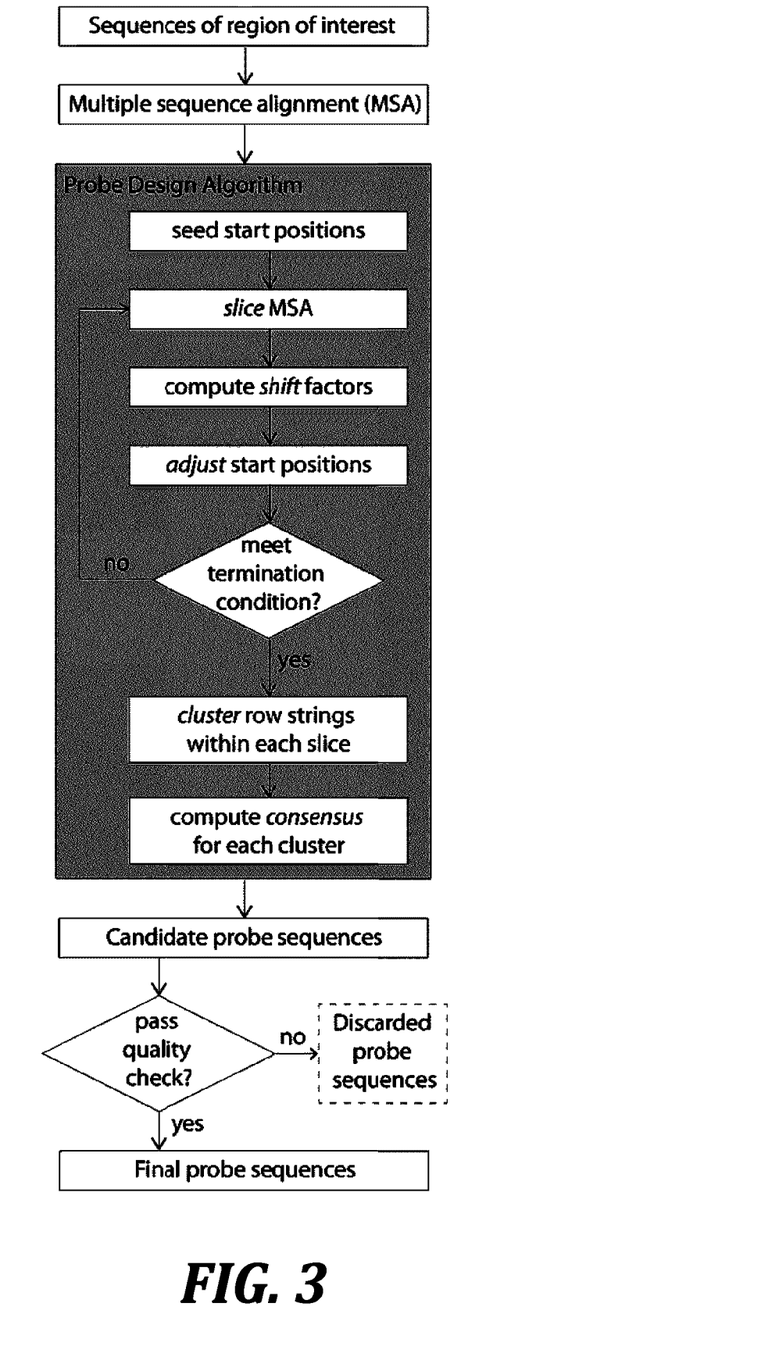
FIG. 3 schematically illustrates an embodiment of the disclosed method and system for providing probe sequences based on an initial, diverse set of sequences for a region of interest.

Next, the MSA resulting from the prior step is taken as input to the design algorithm (see FIGS. 2 and 3). The output of the algorithm is a collection of probe sequences. These probe sequences can be then checked against a sequence database, such as NCBI GenBank, using BLAST (or another search tool) to ensure that they are not highly similar to the nucleic acid sequences of non-target organisms. This quality control step removes the chance that unwanted nucleic acids are captured. Additionally, modifications can be made to the probes. One modification is the chemical modification of probe ends (1) to block sequencing of probes for anti-theft purposes, and (2) to enhance stability of probes for storage. Another modification is to insert unique hairpin sequences into the probe sequences (1) to mitigate probe-to-sample contamination, and (2) to improve target capture efficiency. Specifically regarding target capture, this aspect can be typically performed by the binding between biotin (which is attached to the probe on one end) and streptavidin (which is attached to some surface); more generally, target capture is achieved by the binding between a ligand and a receptor. By introducing a hairpin (see FIG. 4), the biotin can be better positioned to prevent the effects of steric hindrance that reduces biotin-streptavidin binding efficiency (see FIGS. 5A and 5B). Thus, target capture of target nucleic acids can be improved via enhancing biotin-streptavidin (or ligand-receptor) binding efficiency.

In a later step of the disclosed approach, the designed probe sequences are used to synthesize the desired probe constructs. The synthesized probes are used in the target capture step according to any applicable experimental protocols. The target-enriched libraries can be sequenced, for example, using any commercially available NGS approach (such as with instrumentation by Illumina and Life Technologies).

Finally, the read data generated by the NGS machines can be analyzed using known procedures and analytical methods. For example, in the context of sampling influenza HA and NA domains, the obtained reads are mapped to reference sequences for each of the recognized HA and NA subtypes using a read aligner, such as BWA (Li H, Durbin R. 2009. Fast and accurate short read alignment with Burrows-Wheeler Transform. *Bioinformatics* 25:1754-60) or Bowtie2 (Langmead B, Salzberg S L. 2012. Fast gapped-read alignment with Bowtie 2. *Nat Methods* 9:357-9.). Then, the mapping positions of the reads are summarized in depth-of-coverage plots that show how well the reference sequences are sampled by the reads. The reference sequences of well-supported subtypes are expected to be completely or nearly completely covered. The target capture performance of the probes can be assessed using these plots.

The following is a description of an illustrative algorithm for designing the molecular probes capable of sampling and enriching for diverse variants of a target sequence. This description specifically addresses the probe design algorithm indicated as the second step of the disclosed sampling approach (see scheme illustrated in FIG. 1).

Probe Design Algorithm

The problem of designing a collection of molecular probe sequences from an input group of nucleic acid sequences was formulated describe herein.

As a preliminary matter, to assist with the description of the algorithm, several functions are defined that are generalizations of key steps in the algorithm (in various embodiments, the specific functions can be vary, but nonetheless achieve the goals). In practice, these functions can be particular computational techniques (for example, Bayesian clustering can be used for the cluster function) or mathematical functions (for example, the shift function can be defined as deviation of the empirical expectation from the theoretical expectation, assuming a standard normal distribution) as chosen by the user as appropriate. Therefore, the algorithm outlined herein represents a general framework for the design of probe nucleic acids sequences given a collection of nucleic acids sequences of a genetic region of interest. See Modifications for further discussion of particular embodiment variations.

A set of strings S is obtained (its size is denoted by |S|), whose characters belong to the alphabet $\Sigma=\{A, C, G, T\}$. Note that the letter for the nucleotide uracil U is substituted by the letter T.

The strings in S are first aligned against each other using a multiple sequence alignment (MSA) algorithm. The MSA algorithm can be any appropriate algorithm known in the art. Several exemplary embodiments are discussed further in Modification 1 below.

Each row in the MSA represents the transformed version of a string in S after being aligned against all the other strings in S. All rows in the MSA are of the same length L. Gaps (denoted by -), which represent insertions or deletions, can be introduced into the strings in S as a result of the MSA. The set of transformed strings is denoted by S', and its characters belong to the extended alphabet $\Sigma'=\Sigma\cup\{-\}$.

Definition 1: An MSA is an |S| by L matrix whose elements $r_{i,j}$ belong to $\Sigma$ for $i\in\{1, \ldots, |S|\}$ and $j\in\{1, \ldots, L\}$.

The MSA is used as the input of the exemplary algorithm. The algorithm is concerned with the problem of identifying a set of strings P, each of which is a substring of a string in S and of some user-defined length k.

Definition 2: Each string in set P is a substring of a string in S'. It is also a sequence of elements in the MSA, and is denoted by $p_{i,j,k}=r_{i,j},r_{i,j+k-1}$, where $i\in\{1,\ldots,|S|\}$ and $j\in\{1,\ldots,L\}$.

The algorithm identifies intervals in an MSA suitable for probe design. It locates non-overlapping intervals spaced along the MSA that satisfy defined constraints (for details regarding how spatial constraints are met, see Definition 5). See Modification 2 for different spacing schemes. The algorithm then extracts subsets of the MSA that lie within those intervals of length k (called "MSA subsets" or "slices"). The positions leftmost positions (e.g., 5' positions in the nucleic acid sequences) of the slices are called "start positions". For example, in FIG. 2, slices of length 4 are extracted from the MSA, which is consisted of 5 transformed strings.

Definition 3: The function slice(i,k) subsets the MSA into a |S| by i+k−1 matrix (that is, the output slice), where $i\in\{1, \ldots, L\}$.

Next, a shift function is formulated to inform (1) in which direction and (2) to what extent the slices are to be shifted. See Modification 3 for a discussion of various illustrative forms of the shift function. The output of this function is used to optimize the start positions of the slices to, for example, maximize the target percent representation of the transformed strings in the MSA.

Definition 4: The function shift(X) returns a positive or negative value as a function of the matrix X. The sign of the value indicates the direction of shift for the slice.

The shift values are then used to adjust the start positions of the slices. The possible locations of each of the start positions can be constrained. The adjust function applies the shift values to the start positions of the slices, and also checks whether the start positions satisfy spatial constraints. See Modification 4 for alternate adjustment schemes.

Definition 5: The function adjust(X, Y, A, B) takes a list of start positions, X, and alters each start position according to the shift values in Y, while ensuring that the adjusted start positions are within allowable left boundary positions in A and allowable right boundary positions in B. That is, $0\leq a_i\leq x_i+y_i$ and $x_i+y_i+k-1\leq b_i$, where $x_i, y_i, a_i,$ and $b_i$ denote the $i^{th}$ element in X, Y, A, and B, respectively, and $0\leq a_i, b_i\leq L, \forall i\in\{1, \ldots, |X|\}$. Note that X, Y, A, and B are of the same length. The function returns a corresponding list of adjusted start positions.

In each iteration, the probe design algorithm (1) takes start positions, (2) extracts slices beginning at those start positions, (3) computes shift values from the slices, and then (4) adjusts the start positions using the shift values. This procedure is repeated until specified termination conditions are met. The termination conditions can be any determined criteria appropriate for the intended analysis. For example, after a specified number of iterations have been attempted or the maximum shift value is 1 for 5 consecutive iterations. A workflow diagram of the algorithm is depicted in FIG. 3.

Once the start position adjustments are completed, each slice resulting from the new start positions (i.e., also referred to as "adjusted MSA subset") is inputted into the cluster function. See Modification 5 for a brief discussion of illustrative clustering methods. The row strings of the input slice are clustered together by similarity using some distance metric (for example, simple Hamming distance).

Definition 6: The function cluster(X,o) partitions the row strings in the matrix X into groups such that $d(p,q) \leq o$, where $d(p,q)$ denotes the pairwise distance between strings p and q and where o is the maximum allowed distance. It returns groups of similar strings.

For a given slice (adjusted MSA subset), the resulting groups of similar row strings are ranked according to their sizes. The largest groups of row strings that collectively comprise over z (an input parameter) percentage of the strings in S are retained, and the smaller groups can be discarded from the last step. Finally, each group of similar strings retained are then taken as input into the consensus function to create representative strings, which are the probe strings themselves—that is, elements of the set P.

Definition 7: The consensus(X) function takes a matrix X and returns a string with characters $c_1 c_2 \ldots c_k$, where $c_i$ is the most frequently observed character at column i in the matrix. The output string is simply the majority-rule consensus sequence. Note that gaps should be removed from the consensus sequence.

In summary, supplied with the above definitions, a probe design algorithm is formulated to determine P given an input MSA and two input parameters k (probe length) and z (minimum percentage).

Quality Check

The raw output of the probe design algorithm described herein is a collection of probe nucleic acids sequences for targeted high-throughput sequencing. These probe sequences are preferably checked against a nucleic acids sequence database, such as NCBI GenBank, using a search tool, such as BLAST, to ensure that the probe sequences are not highly similar to reported nucleic acids sequences belonging to non-target organisms. For example, for probes designed to target the influenza genome, potential probe sequences that display high sequence identity (for example, over 75%) to any non-influenza nucleic acids sequences in NCBI GenBank are preferably discarded prior to application of the probes. The remaining probe sequences can then be considered quality-checked. Additionally, one may perform a BLAST check to ensure that the final probe sequences (which are built as consensus sequences and therefore may not be exactly the same as previously recorded natural sequences) exhibit high sequence similarity to known influenza nucleic acids sequences.

Modifications

In various embodiments, the steps in the probe design algorithm can be modified to enhance probe design and/or to adapt the algorithm to particular problems or circumstances. Several exemplary modifications are described below. However, it will be appreciated that additional modifications may exist that can be utilized for the same or similar purposes according to ordinary skill in the art.

Exemplary Modification 1—Multiple Sequence Alignment Methods

Various tools have been published in the bioinformatics literature to address the classical problem of aligning a set of nucleotide (or amino acid) sequences against each other. The product of these tools is a MSA matrix, whose columns represent homologous positions of the sequences. Commonly used aligners include ClustalW (Larkin M A, et al. 2007. ClustalW and ClustalX version 2. *Bioinformatics* 23:2947-8), MAFFT (Katoh K, Standley D M. 2013. MAFFT multiple sequence alignment software version 7: improvements in performance and usability. *Mol Biol Evol* 30:772-80), MUSCLE (Edgar R C. 2004. MUSCLE: multiple sequence alignment with high accuracy and high throughput. *Nucleic Acids Res* 32:1792-7), and ProbCons (Do C B, Mahabhashyam M S P, Brudno M, and Batzoglou S. 2005. PROBCONS: Probabilistic Consistency-based Multiple Sequence Alignment. *Genome Res* 15:330-40). These aligners have varying accuracies and speeds. Some are better at handling large data sets or more difficult data sets (for example, more divergent sequences) than others. The user may wish to use the aligner most appropriate for the data set being analyzed. In principle, however, any aligner could be used, but it must be emphasized that the quality of the MSA may impact the output of the probe design algorithm.

Exemplary Modification 2—Initial Spacing Schemes

The start positions can be initially seeded using simple heuristics. For example, uniform spacing along the entire length of MSA. However, one may devise more complex schemes to optimize spacing between slices. For instance, two slices can first be placed at the ends of the MSA, and then the remaining slices can be spaced evenly along the unoccupied length of the MSA. Another possibility is to use structural information in the MSA in order to locate relatively conserved regions to place initial slices.

Exemplary Modification 3—Shift Functions

The purpose of a shift function is to determine how to adjust the position of a slice based on the contents of the slice. Suppose that one wishes to place slices such that their nucleotide sequences are relatively conserved. One formulation of the shift function is the "center of mass". The idea is to shift a slice such that the center of mass of the entropy (or conservation) landscape of the sequences (which is viewed as a body of mass here) in the slice is as close to the midpoint of the slice as possible. The information in the slice can be captured using different formulations other than entropy and conservation. The shift function can be defined in various ways, so long as it helps to find locations for the slices optimal for the intended objective (for example, to minimize the number of probes generated per slice).

Exemplary Modification 4—Start Position Adjustment Schemes

In one embodiment, the probe design algorithm sequentially refines the start positions. The algorithm greedily iterates through the positions in an ascending order. However, the user may find other ordering schemes to be more useful or desirable. For example, one may randomize the starting positions to refine. This may influence the placement of the start positions if it is required that the slices should be at least some specified distance apart (that is, defining allowable slice boundaries based on the starting positions of flanking slices, which may change from iteration to iteration).

Exemplary Modification 5—Clustering Methods

There is a large and growing suite of clustering algorithms in the machine learning literature. A classical hierarchical clustering method can be used to find groups of similar strings based on a distance metric, such as the Hamming distance (variants of the Hamming distance or other types of distance metrics can also be used). More sophisticated methods such as Bayesian hierarchical clustering can be applied instead, which yield probabilistic thresholds for grouping strings. In principle, any clustering algorithm can be adapted to bin strings into separate groups. The key information from clustering are (1) the number of groups to separate the strings into and (2) which strings fall into each of the groups. It is up to the user to explore various clustering algorithms and to decide which is most fit to group the sequence data at hand.

It is noted that, as used herein, the use of the term "or" in the claims means "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

The following is a proof-of-concept description of an illustrative application of the disclosed system and methods to generate novel probes that effectively enrich and sequence diversity of influenza virus from clinical samples.

Introduction: The approach described herein can overcome target capture bias in targeted sequencing applications. The disclosed approach is especially advantageous for applications where the target genetic region exhibits notable heterogeneity. Also described herein, the disclosed approach was applied to the enrichment and sequencing of the influenza virus genome, which is typically found in minute amounts in clinical samples. Target capture using conventionally designed probes is biased towards single reference or consensus sequences. As such, existing probe designs do not account for the rapidly mutating nature of the target nucleic acids. When the target molecules differ substantially from the probes, enrichment is reduced and biased towards molecules more similar to the probes. The present approach overcomes this problem by taking into account the known sequence universe of the target genetic region, and produces a pool of probes that cover a broader and more comprehensive spectrum of variants of the targeted genetic region. The disclosed system is, thus, optimal for cases where abundant sequence data are available from private and/or public sources (for example, influenza). The rational, data-driven designed probes, when combined with the best target enrichment techniques and sequencing machines, offer a way to capture target nucleic acids with mitigated target capture bias and improved detection sensitivity when the target exhibits significant sequence diversity.

Results and Discussion: Probes targeting two rapidly mutating segments of the influenza virus, namely segments HA and NA were designed and synthesized. Publicly available sequence data (from the NCBI Influenza Virus Resource) were downloaded, curated, and then used as input to the probe design algorithm part of this disclosure. Probe sequences were generated for each known subtype of HA (H1 to H16) and NA (N1 to N9), and then manually checked prior to probe synthesis. The probes were ordered through a commercial oligonucleotide manufacturer. The entire procedure was performed using the newly designed probes in the target capture step on three culture-based samples (a single strain of H3N2; a mixture of two H1N1 strains and one H3N2 strain; and a negative control with no influenza virus). For each of these culture-based samples, a series of dilution levels were created to test the sensitivity of the target capture step: 100%, 10%, and 1% of the supplied material. For the NGS step, all 9 samples (3 dilution levels for each of the 3 specimens) were sequenced on the Illumina MiSeq machine. After basic quality control steps, the resulting Illumina reads were mapped to representative reference sequences for each of the 16 HA and 9 NA subtypes. The results indicate that the probes are effectively pulling out desired influenza HA and NA segments straight from the samples, even at the lowest dilution level of 1%. These preliminary experiments demonstrate that the probes designed using available sequence data can enrich for the target nucleic acids and can do so with high sensitivity. Additional experiments can be conducted to further affirm and demonstrate the utility of the disclosed system and methods on additional clinical specimens and its superior performance over targeted sequencing using conventional probes, as well as whole metagenome sequencing without target enrichment.

While illustrative embodiments have been illustrated and described, it will be appreciated that various changes can be made therein without departing from the spirit and scope of the invention.

---

The embodiments of the invention in which an exclusive property or privilege is claimed are defined as follows:

1. A method of isolating a plurality of nucleic acid sequences of a targeted genomic domain from a sample, comprising:
   (a) providing a multiple sequence alignment (MSA) of nucleic acid sequences of the targeted genomic domain;
   (b) designing a plurality of representative subsequences, comprising:
      (i) designating a plurality of intervals within the length of the MSA, wherein each interval consists of an MSA subset with aligned nucleic acid subsequences of the observed variants, and wherein each MSA subset has a distinct start position;
      (ii) independently shifting the start position for each MSA subset within the MSA by a designated number of nucleic acid positions and in a designated direction to provide an adjusted MSA subset with aligned adjusted nucleic acid subsequences of the observed variants;
      (iii) independently assessing each adjusted MSA subset for conformance to a termination criterion and repeating step (ii) if an adjusted MSA does not conform to the termination criterion;

(iv) independently clustering the aligned nucleic acid subsequences within each adjusted MSA subset into separate groups;

(v) forming a reduced MSA subset corresponding to each adjusted MSA subset by including only groups in the adjusted MSA subset that meet or exceed a preset size threshold;

(vi) determining a representative subsequence for each group; and (c) contacting a plurality of probes to the sample, wherein each probe comprises the representative subsequence, or the complement thereof, of a reduced MSA subset; and (d) isolating the nucleic acid molecules in the sample that hybridize to one or more probes of the plurality of probes.

2. The method according to claim 1, wherein the plurality of intervals within the length of the MSA are designated according to defined spatial constraints.

3. The method according to claim 2, wherein the designated intervals are distributed uniformly across the length of the MSA or wherein the plurality of intervals within the length of the MSA are designated in areas that contain above average conservation within the MSA.

4. The method of claim 1, wherein at least two of the plurality of representative subsequences are non-overlapping or wherein the plurality of intervals in step (b)(i) are designated randomly.

5. The method of claim 1, wherein the designating of step (b)(i) comprises extracting the MSA subsets from the plurality of designated intervals to provide the aligned nucleic acid subsequences within each designated interval; or wherein the designated number of nucleic acid positions by which each MSA subset start position is shifted does not exceed the length of the respective MSA subset; or wherein the adjusted MSA subsets resulting from the shifting of step (b)(ii) conform to defined spatial constraints; or wherein the termination criterion of step (b)(iii) comprises a preset number of shift iterations, a preset percentage of conserved positions within the adjusted MSA subset, a preset threshold for positioning of conserved positions, and the like; or where the sequences of the MSA are first transformed to have the same length by inserting gaps in the shorter sequences in a manner that enhances alignment of homologous nucleic acids in the MSA.

6. The method of claim 1, wherein the start position of each MSA subset is: a position that is at the 5' end or the 3' end of the subset; shifted in the 5' direction, or shifted in the 3' direction.

7. The method of claim 1, wherein the designated number of nucleic acid positions and/or the designated direction for independently shifting each MSA subset increases the number of conserved positions within the adjusted MSA subset or increases the placement of the conserved positions within a center region of the adjusted MSA subset.

8. The method of claim 1, wherein the clustering of step (b)(iv) includes executing an algorithm that groups the adjusted nucleic acid subsequences of each adjusted MSA subset by similarity using a distance metric to provide one or more groups of adjusted nucleic acid subsequences for each adjusted MSA subset.

9. The method of claim 8, wherein the clustering of step (b)(iv) further comprises ranking the one or more groups of adjusted nucleic acid subsequences for each adjusted MSA subset according to size as defined by number of adjusted nucleic acid subsequences.

10. The method of claim 1, further including denoising the reduced MSA subset of any spurious variants.

11. The method of claim 10, wherein the representative sequence is a consensus sequence for the corresponding reduced MSA subset.

12. The method of claim 1, wherein the representative sequence for each reduced MSA subset is screened in silica against a database of known nucleic acid sequences, wherein any representative sequence that demonstrates high similarity to a known sequence irrelevant to the target genomic domain is omitted from further steps in the method.

13. The method of claim 1, wherein at least one probe comprises the representative sequence, or the complement thereof, is not continuous within the at least one probe.

14. The method of claim 13, wherein the representative sequence, or the complement thereof, within at least one probe is interrupted by a sequence that facilitates formation of a hairpin structure.

15. The method of claim 1, wherein each representative sequence is included in at least one probe within the plurality of probes.

16. The method of claim 1, further comprising sequencing the nucleic acid molecules isolated from the sample.

* * * * *